(12) United States Patent
Dumenil et al.

(10) Patent No.: US 8,158,833 B2
(45) Date of Patent: Apr. 17, 2012

(54) PROCESS, PLANT AND BUTANOL FROM LIGNOCELLULOSIC FEEDSTOCK

(75) Inventors: Jean-Charles Dumenil, Little Chalfont (GB); Ian Dobson, London (GB)

(73) Assignee: BP Biofuels UK Ltd., Middlesex (GB)

( * ) Notice: Subject to any disclaimer, the term of this patent is extended or adjusted under 35 U.S.C. 154(b) by 459 days.

(21) Appl. No.: 12/337,024

(22) Filed: Dec. 17, 2008

(65) Prior Publication Data

US 2010/0152496 A1 Jun. 17, 2010

(51) Int. Cl.
*C07C 31/12* (2006.01)
*C12P 7/16* (2006.01)

(52) U.S. Cl. .................. 568/840; 435/160; 435/289

(58) Field of Classification Search .................. 568/840; 435/160, 289.1
See application file for complete search history.

(56) References Cited

U.S. PATENT DOCUMENTS

| | | | |
|---|---|---|---|
| 4,612,286 | A | 9/1986 | Sherman et al. |
| 5,221,357 | A | 6/1993 | Brink |
| 7,098,009 | B2 | 8/2006 | Shanmugam et al. |
| 7,309,602 | B2 | 12/2007 | David |
| 2002/0069987 | A1 | 6/2002 | Pye |
| 2004/0231661 | A1 | 11/2004 | Griffin et al. |
| 2007/0099278 | A1 | 5/2007 | Aare |
| 2008/0033188 | A1 | 2/2008 | Dumesic et al. |
| 2008/0050800 | A1 | 2/2008 | McKeeman et al. |
| 2008/0057555 | A1 | 3/2008 | Nguyen |
| 2008/0160593 | A1 | 7/2008 | Oyler |
| 2008/0227182 | A1 | 9/2008 | Anderson et al. |

FOREIGN PATENT DOCUMENTS

| | | |
|---|---|---|
| BR | 9706137 | 12/1997 |
| JP | 2009 183806 | 8/2009 |
| WO | WO 2007/095215 A2 | 8/2007 |
| WO | WO 2007/112090 A2 | 10/2007 |
| WO | WO 2008/045977 A2 | 4/2008 |
| WO | WO 2008/053284 A1 | 5/2008 |
| WO | WO 2008/060595 A2 | 5/2008 |
| WO | WO 2008/095033 A2 | 8/2008 |
| WO | WO 2008/151149 A2 | 12/2008 |
| WO | WO 2008/156651 A1 | 12/2008 |

OTHER PUBLICATIONS

H. Jorgensen, et al., "Enzymatic Conversion of Lignocellulose into Fermentable Sugars: Challenges and Opportunities," Published online Jun. 27, 2007, Wiley InterScience (www.interscience.wiley.com); DOI: 10.1002/bbb.4: Biofuels, Bioprod. Bioref. 1:119-134 (2007).

B. Yang et al. "Pretreatment: the Key to Unlocking Low-Cost Cellulosic Ethanol," Published online Dec. 17, 2007 in Wiley InterScience (www.interscience.wiley.com); DOI: 10.1002/bbb.49, Biofuels, Bioprod. Bioref. 2:26-40 (2008).

Y. Chin-Chung et al., "Enzymatic Saacharification and Fermentation of Xylose-Optimized Dilute Acid-Treated Lignocellulosics", Human Press Inc., vol. 121-124, 2005, pp. 947-961.

D. Chuan-Chao et al., "Biodiesel Generation From Oleaginous Yeast *Rhodotorula glutinis* with Xylose Assimilating Capacity", African Journal, Sep. 19, 2007, pp. 2130-2134.

E. Easterling et al. "The Effect of Glycerol as a Sole and Secondary Substrate on the Growth and Fatty Acid Composition of *Rhodotorula glutinis*", Published Elsevier 2008, Bioresource Technology, pp. 356-361.

J. Fein et al. "Evaluation of D-Xylose Fermenting Yeasts for Utilization of Wood-Derived Hemocellulose Hydrolysate", Western Research Center, Feb. 7, 1984, pp. 682-690.

S. Lemmel et al. "Fermentation of Xylan by *Clostridium acetobutylicum*", Enzyme Microb Technol, Oct. 3, 1985, pp. 217-221.

R. Marchal et al. "Large-Scale Enzymatic Hydrolysis of Agricultural Lignocellulosic Biomass. Part 2: Conversation into Acetone-Butanol", Bioresource Technologies, Jan. 24, 1992, pp. 205-217.

M. Mes-Hartree et al. "Butanol Production of *Clostridium acetobutylicum* Grown on Sugars Found in Hemicellulose Hydrolysates", Biotechnology Letters vol. 4 (1982) pp. 247-252.

N. Qureshi et al.; Butanol, 'a superior biofuel' Production From Agricultural Residues (renewable biomass): Recent progress in Technology† Biofpr, Mar. 3, 2008, pp. 319-330.

I.C. Roberto et al. "Utilization of Sugar Cane Begasse Hemicellulosic Hydrolysate by *Pichia stipitis* for the Production of Ethanol", Process Biochemistry, Aug. 14, 1990, pp. 15-21.

D. Savage et al. "Defossilling Fuel: How Synthetic Biology Can Transform Biofuel Production", ACS Chemical Biology vol. 3, Jan. 18, 2008, pp. 13-16.

D.R. Woods, "The Genetic Engineering of Microbial Solvent Production", Elsevier Science Ltd., Jul. 1995 pp. 259-264.

*Primary Examiner* — Sikarl Witherspoon

(74) *Attorney, Agent, or Firm* — John P. Poliak

(57) ABSTRACT

This invention relates to a process, a plant, and butanol made of or derived from lignocellulosic feedstock. The process includes the step of depolymerizing lignocellulosic material to form pentose and a remainder. The process also includes the step of converting the pentose to butanol material and using the remainder for generation of power or further downstream conversion.

13 Claims, 2 Drawing Sheets

PROCESS, PLANT AND BUTANOL FROM LIGNOCELLULOSIC FEEDSTOCK

BACKGROUND

1. Technical Field

This invention relates to a process, a plant, and butanol made of or derived from lignocellulosic feedstock.

2. Discussion of Related Art

Tightening oil supply and escalating energy prices along with environmental concerns over nonrenewable resources have prompted significant interest and research into alternative fuels. Efforts to reduce carbon emissions and greenhouse gases are also driving investment into alternative fuels.

Anderson et al., U.S. Patent Application Publication 2008/0227182 discloses systems and methods for enzymatic hydrolysis of lignocellulosic materials. The enzymatic hydrolysis converts hexose sugars from cellulose and pentose sugars from hemicellulose. The system produces a mixed stream of 6-carbon sugars and 5-carbon sugars and then seeks to ferment them to ethanol with a microorganism capable of fermenting both glucose and xylose to ethanol. Anderson et al. does not disclose segregated 6-carbon sugar and 5-carbon sugar processes.

McKeeman et al., U.S. Patent Application Publication 2008/0050800, discloses a method and apparatus for a multi-system bioenergy facility. The multi-system bioenergy facility generates electricity with biogas from an anaerobic digester and ethanol from an ethanol production facility. The multi-system bioenergy facility also generates triglycerides with algae from bioreactors supplied with nutrient rich waste water from the anaerobic digester and carbon dioxide rich flue gas from a steam production facility. McKeeman et al. does not disclose a sugar to biodiesel method or apparatus.

Aare, U.S. Patent Application Publication 2007/0099278, discloses production of biodiesel from a combination of corn (maize) and other feed stocks. The process separates corn oil and corn starch which is enzymatically converted to fermentable sugars with a liquification and saccharification process. Yeast is added to ferment the sugars before distillation to produce ethanol. The corn oil is fed into a transesterification vessel where ethanol with catalyst forms crude biodiesel and crude glycerin. The amount of biodiesel is limited to the small amount of oil in the corn. Aare does not disclose a sugar to biodiesel process.

However, even with the above improvements in the processes, there is a need and a desire to produce butanol from a lignocellulosic feedstock. There is a need and a desire for a process or a plant to produce butanol in a manner that is less expensive and more efficient than known processes. There is also a need and a desire for a pentose only conversion process.

SUMMARY

This invention relates to a process, a plant, and butanol made of or derived from lignocellulosic feedstock. In a broad embodiment, this invention includes production of butanol from pentose, such as from hemicellulose material. Desirably, hexose from the feedstock and/or from cellulose in the feedstock may be processed separately, such as not to compete with pentose consumers.

The invention also includes using inexpensive lignocellulosic feedstock to produce butanol. The lignocellulosic feedstock provides a source of extractable pentose from the hemicellulose. The pentose provides the building components to produce butanol, such as by a biological or chemical pathway. The balance or remainder after pentose extraction can be treated to extract additional hexose from the cellulose or can be burned to produce energy or power.

This invention includes a process or a plant to produce butanol in a manner that is less expensive and more efficient than known processes. This invention also may also include a pentose only conversion process, such as without a substantial amount of hexose.

According to a first embodiment, this invention includes a process for producing butanol from lignocellulosic feedstocks. The process includes the step of depolymerizing pentose from a lignocellulosic feedstock to form a remainder, and the step of converting the pentose to butanol.

According to a second embodiment, this invention includes a butanol plant for producing butanol from a lignocellulosic feedstock. The plant includes a lignocellulosic feed system, a pentose depolymerization unit adapted for removing pentose from the lignocellulosic feedstock to form a remainder. The plant also includes a pentose conversion unit adapted for converting pentose to butanol.

According to a third embodiment, this invention includes butanol and/or biofuel material made by the processes or manufacturing plants described herein. The biofuel material includes biogasoline and/or biodiesel.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention. In the drawings.

DETAILED DESCRIPTION

The invention may cover or include a process of converting a lignocellulosic feedstock into hydrocarbons and/or oxygenated hydrocarbons for the use in biofuel applications, such as butanol.

The process may include extracting or removing pentose from the lignocellulosic feedstock, such as pentose originally in the hemicellulose part of the feedstock. The process may also include forming a pentose or sugar stream and a remainder, such as made of cellulose and lignin. The pentose stream can be converted into hydrocarbons or oxygenated hydrocarbons, such as using fermentation processes based on single cell organisms or microorganisms to butanol. The remainder may be used for a secondary step of conversion and/or burned for energy.

According to one embodiment, this invention focuses on the use of pentose ($C_5$ sugars) for the production of biofuels by fermentation while hexose ($C_6$ sugars) can be left in the material and either sent to the boiler for generating power used in the process, or processed further to make another component or biofuel. Desirably, this invention includes using only the $C_5$ sugars for the fermentation process, such as to reduce complexity and costs of processing and related equipment. The remainder may include sufficient material to generate the energy necessary for the conversion process, or the remainder may be used as a feedstock for secondary conversions or applications. The $C_5$ sugar stream from the feedstock may provide the building blocks for the biofuel and a $C_6$ sugar stream including cellulose may be processed as a waste stream.

The process may include the step of extracting the pentose from the lignocellulosic feedstock and the step of forming a sugar stream and a residue. The $C_5$ sugar stream can then be converted into a hydrocarbon or an oxygenated hydrocarbon using fermentation processes, such as butanol. The residue can be used for a secondary step of conversion (power and/or hydrocarbon or/and oxygenated hydrocarbons).

Figure 1:
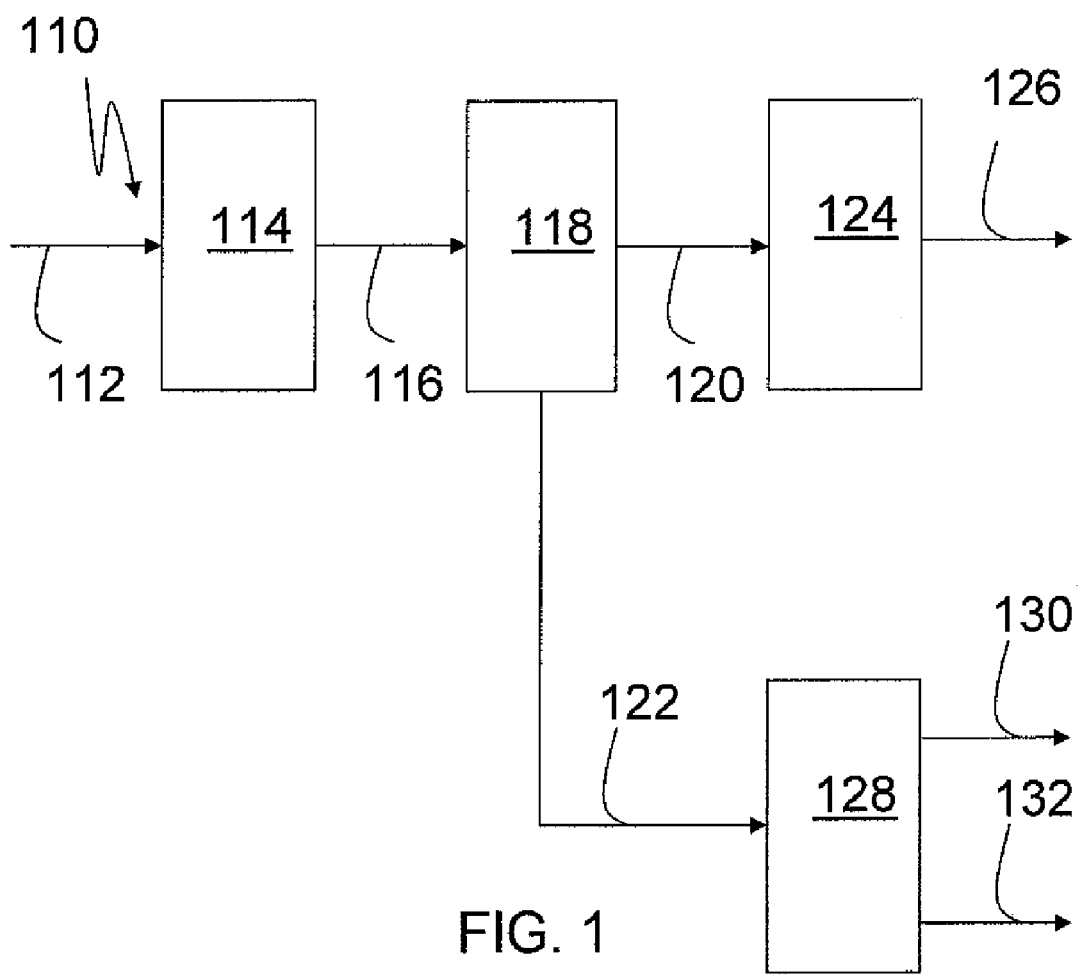
FIG. 1 illustrates a butanol plant with a powerhouse, according to one embodiment.

FIG. 1 shows a butanol plant 110 with a powerhouse 128. The plant 110 includes a feedstock line 112 connected to a feed system 114. The feed system 114 connects to a lignocellulosic feedstock line 116. The lignocellulosic feedstock line 116 connects to a pentose depolymerization unit 118. The pentose depolymerization unit 118 produces pentose by a pentose line 120 and a remainder by a remainder line 122. The pentose line 120 connects to a pentose conversion unit 124 to produce butanol by a butanol line 126. The remainder line 122 connects to the powerhouse 128 to produce steam by a steam line 130 and/or electricity by an electricity line 132.

Figure 2:
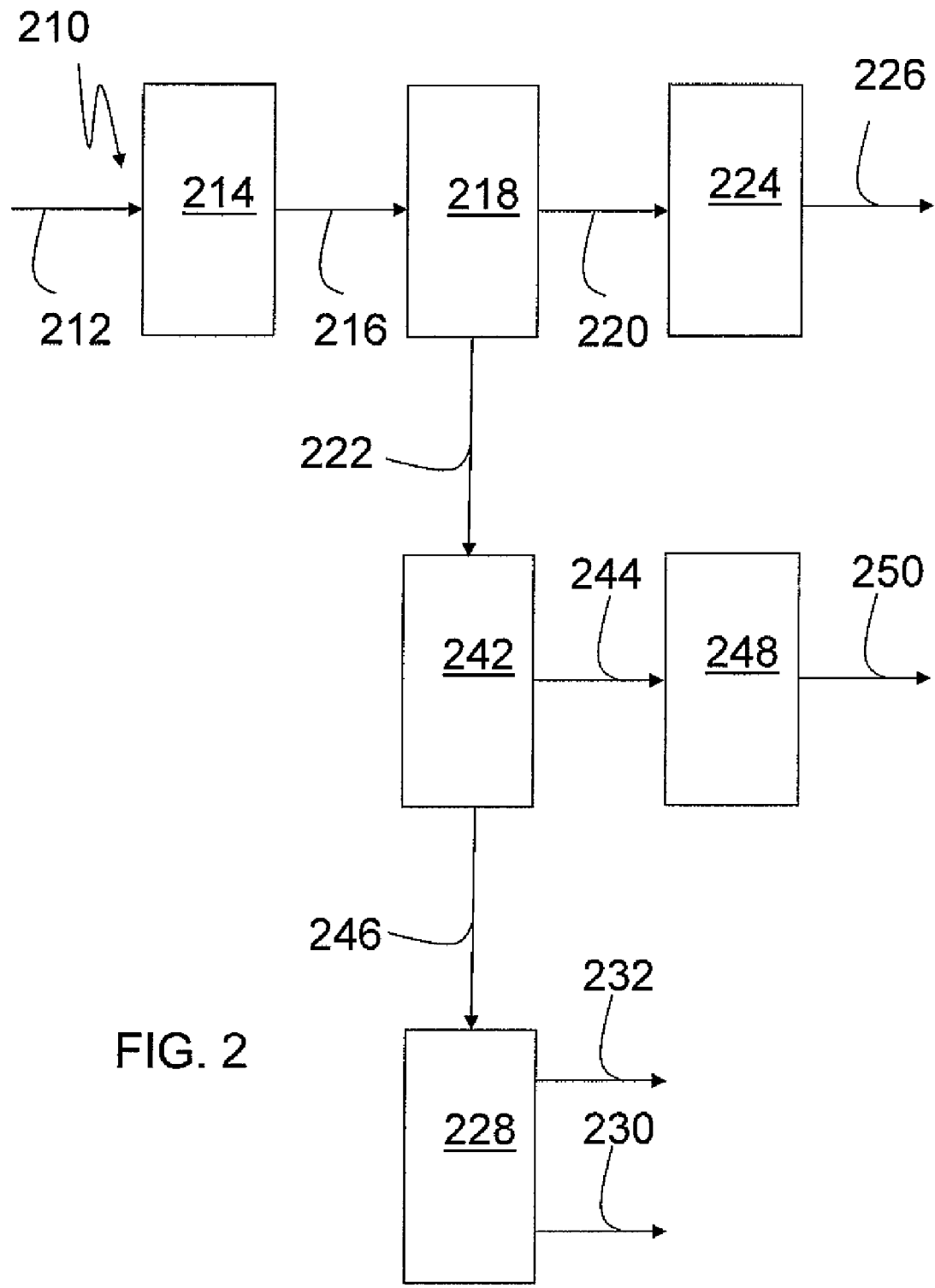
FIG. 2 illustrates a butanol plant with a hexose conversion unit, according to one embodiment.

FIG. 2 shows a butanol plant 210 with a hexose conversion unit 248. The plant 210 includes a feedstock line 212 connected to a feed system 214. The feed system 214 connects to a lignocellulosic feedstock line 216. The lignocellulosic feedstock line 216 connects to a pentose depolymerization unit 218. The pentose depolymerization unit 218 produces pentose by a pentose line 220 and a remainder by a remainder line 222. The pentose line 220 connects to a pentose conversion unit 224 to produce butanol by a butanol line 226. The remainder line 222 connects to a hexose depolymerization unit 242. The hexose depolymerization unit 242 produces hexose by a hexose line 244 and a reduced remainder by a reduced remainder line 246. The hexose line 244 connects to a hexose conversion unit 248, such as a same or a different fermentor as the pentose conversion unit 224. The hexose conversion unit 248 produces a biofuel by a second biofuel line 250, such as biogasoline and/or biodiesel. Optionally, the reduced remainder line 246 connects to a powerhouse 228 to produce steam by a steam line 230 and/or electricity by an electricity line 232.

According to one embodiment, this invention may include a process for producing butanol from lignocellulosic feedstocks. The process may include the step of depolymerizing pentose from a lignocellulosic feedstock to form a remainder, and the step of converting the pentose to a butanol.

Biofuel broadly refers to components or streams suitable for use as a fuel or a combustion source derived from renewable sources, such as may be sustainably produced and/or may have reduced or no net carbon emissions to the atmosphere. Biofuel broadly includes biogasoline materials or products and/or biodiesel materials or products. Renewable resources may exclude materials mined or drilled, such as from the underground. Desirably, renewable resources may include single cell organisms, microorganisms, multicell organisms, plants, fungi, bacteria, algae, cultivated crops, non-cultivated crops, and/or the like.

Biogasoline broadly refers to components or streams suitable for blending into the gasoline or octane pool or supply derived from renewable sources, such as methane, hydrogen, syn (synthesis) gas, methanol, ethanol, propanol, butanol (all isomers), dimethyl ether, methyl tert-butyl ether, ethyl tert-butyl ether, hexanol, aliphatic compounds (straight, branched, and/or cyclic), heptane, isooctane, cyclopentane, aromatic compounds, ethyl benzene, and/or the like. Butanol broadly refers to products and derivatives of 1-butanol, 2-butanol, iso-butanol, other isomers, and/or the like. Biogasoline may be used in spark ignition engines, such as automobile gasoline internal combustion engines. According to one embodiment, the biogasoline and/or biogasoline blends meet or comply with industrially accepted fuel standards.

Desirably, biogasoline or biogasoline material may be used by itself and/or blended with other fuels, such as mineral oil based hydrocarbons or refinery produced products. Biogasoline blends may include any suitable amount by volume of biogasoline, such as at least about 5 percent, at least about 10 percent, at least about 15 percent, at least about 20 percent, at least about 30 percent, at least about 40 percent, at least about 50 percent, at least about 60 percent, at least about 70 percent, at least about 80 percent, at least about 85 percent, at least about 90 percent, at least about 95 percent, about 100 percent, and/or the like.

Alcohol broadly refers to an organic compound in which a hydroxyl group (—OH) binds to a carbon atom of an alkyl or substituted alkyl group. Alcohols may include the general formula of $C_nH_{2n}+1OH$ where n includes any suitable integer, such as 1, 2, 3, 4, 5, 6, 7, 8, 9, 10, 20, 50, and/or the like. Alcohol, as defined in context of this specification, may include methanol, ethanol, propanol, butanol (all isomers), hexanol, and/or the like. According to one embodiment, the process may produce one or more types of alcohol, such as in a combined fermentor and/or in individual fermentors.

Biodiesel or biodiesel material broadly refers to components or streams suitable for blending into the diesel or cetane pool or supply derived from renewable sources, such as fatty acids, fatty acid esters, triglycerides, lipids, fatty alcohols, alkanes, alkenes, pure hydrocarbons, oxygenated hydrocarbons, naphthas, distillate range materials, paraffinic materials, aromatic materials, aliphatic compounds (straight, branched, and/or cyclic), and/or the like. Biodiesel may also refer to aviation fuels (jet), lubricant base stocks, kerosene fuels, and/or the like. Biodiesel may be used in compression engines, such as automotive diesel internal combustion engines. In the alternative, the biodiesel may also be used in gas turbines, heaters, and/or the like. According to one embodiment, the biodiesel and/or biodiesel blends meet or comply with industrially accepted fuel standards.

Desirably, biodiesel, biodiesel material, and/or biodiesel product may be used by itself and/or blended with other fuels, such as mineral oil based hydrocarbons or refinery produced products. Biodiesel blends may include any suitable amount by volume of biodiesel, such as at least about 2 percent, at least about 5 percent, at least about 10 percent, at least about 15 percent, at least about 20 percent, at least about 30 percent, at least about 40 percent, at least about 50 percent, at least about 60 percent, at least about 70 percent, at least about 80 percent, at least about 85 percent, at least about 90 percent, at least about 95 percent, about 100 percent, and/or the like.

Biodiesel material may also include finished and/or intermediate compounds suitable for use as diesel fuel, kerosene fuel, heating fuel, aviation fuel, and/or the like. According to one embodiment, the biodiesel material may include polyunsaturated fatty acids, esters, fatty acid alkyl esters (FAAE), fatty acid methyl esters (FAME), fatty acid ethyl esters (FAEE), triglycerides, alkanes, lipids, and/or the like. Desirably, but not necessarily, the biodiesel material may exclude materials derived from natural oil or essential oils, such as from plants like rapeseed, soy beans, and/or the like.

The biodiesel product may include any suitable material, such as fatty acid esters, other compounds within commercial or industrial diesel specifications, other compounds within aviation fuel specifications, other compounds within kerosene specifications, and/or the like. Biodiesel may include molecules having oxygen, such as for generally cleaner combustion. In the alternative, the biodiesel product may exclude oxygen containing molecules.

Lignocellulosic feedstock broadly refers to any suitable organic material with at least a portion of hemicellulose. Lignocellulosic feedstocks may broadly include bagasse, sugar cane bagasse, energy cane bagasse, rice straw, wheat straw, corn stover, maize stover, sorghum stover, sweet sorghum stover, cotton remnant, sugar beet pulp, miscanthus, switchgrass, other grasses, wood, softwood, hardwood, wood waste, sawdust, paper, paper waste, agricultural waste, municipal waste, sugarcane, energy cane, corn, maize, sorghum, sweet sorghum, sugar beet, rice, cassava, any other suitable biomass material and/or the like. Energy cane broadly refers to grasses that have less soluble sugar than sugar cane and an increased fiber content. Feedstocks may include food materials for human or cattle consumption. In the alternative, feedstocks may exclude food materials for human or cattle consumption, such as switchgrass. Feedstocks desirably may include plant matter, algae, invertebrate animals, vertebrate animals and/or the like. According to one embodiment, feedstocks may include soybeans, rapeseed, jatropha, and/or the like. In the alternative, feedstocks may exclude relatively high oil bearing or oil containing materials.

Carbohydrates broadly refer to compounds having the general formula $C_xH_{2x}O_x$ where x includes any suitable integer, such as 1, 2, 3, 4, 5, 6, 7, 8, 9, 10, 20, 50, and/or the like. Other chemical formulas for carbohydrates and/or sugars are within the scope of the invention. Sugars broadly refer to carbohydrate compounds having a generally at least somewhat sweet sensation on the tongue. Sugars may be building blocks or components of more complex molecules, such as starches, hemicellulose, cellulose, and/or the like.

Lignocellulosic feedstock or material may include lignin, hemicellulose, pectin, cellulose, starch, soluble sugar and/or the like. Lignocellulosic material or lignocellulose may include tightly bound carbohydrate polymers, such as cellulose and hemicellulose combined with lignin by hydrogen bonding and/or covalent bonding, for example. Polymers or polymer form refers to having many repeating units.

Lignin broadly refers to a biopolymer that may be part of secondary cell walls in plants, such as a complex highly cross-linked aromatic polymer that covalently links to hemicellulose. Hemicellulose broadly refers to a branched sugar polymer composed mostly of pentoses, such as with a generally random amorphous structure and up to hundreds of thousands of pentose units. Cellulose broadly refers to an organic compound with the formula $(C_6H_{10}O_5)_z$ where z includes any suitable integer. Cellulose may include a polysaccharide with a linear chain of several hundred to over ten thousand hexose units and a high degree of crystalline structure, for example. Depolymerizing cellulose to hexose may include more severe and/or harsher conditions than depolymerizing hemicellulose, such as due to the crystalline structure of the cellulose.

Depolymerizing broadly refers to taking something larger and breaking it into smaller units or pieces, such as from a long chain molecule with repeating units or structures. Depolymerizing may include breaking or severing chemical bonds, such as to release monomers (1 unit) from a polymeric backbone or chain. Depolymerizing may also produce dimers (2 units), trimers (3 units), tetramers (4 units), any other suitable oligomers (few units), and/or the like, such as intermediates and/or compete products.

Depolymerizing may be done by any suitable mechanism, such as a hydrolysis process, an acidic process (pH 7 and below), a basic or alkali process (pH above 7), an enzymatic process, a solvent process, a thermo-mechanical process, and/or the like. Acid processes may include concentrated and/or dilute acid steps, such as with sulfuric acid, sulfurous acid, hydrochloric acid, phosphoric acid, organic acids, and/or the like. Basic processes may include caustic materials, such as ammonia, calcium hydroxide, calcium oxide, magnesium hydroxide sodium hydroxide, potassium hydroxide, sodium carbonate, potassium carbonate, sodium bicarbonate, potassium bicarbonate, and/or the like. One or more depolymerizing processes may be combined for a synergistic result.

Desirably, but not necessarily, the depolymerizing step results in a stream comprising primarily pentose, such as without a significant amount of hexose. The pentose content may be at least 70 percent of the total sugars from depolymerizing, at least 80 percent of the total sugars from depolymerizing, at least 85 percent of the total sugars from depolymerizing, at least 90 percent of the total sugars from depolymerizing, at least 95 percent of the total sugars from depolymerizing, at least 98 percent of the total sugars from depolymerizing, at least 99 percent of the total sugars from depolymerizing, about 100 percent of the total sugars from depolymerizing, and/or the like.

Pentose broadly refers to five (5) carbon member sugars or saccharides (monomers), corresponding disaccharides (dimers), corresponding trisaccharides (trimers), corresponding tetrasaccharides (tetramers), and/or the like. Pentose includes xylose, ribose, arabinose, ribulose, xylulose, lyxose, any other isomer of five carbon sugars, and/or the like. Desirably, at least a portion of pentose may be separated or derived from the hemicellulose. Pentose may include or form complexes of relatively simple sugars, such as a disaccharide and/or a trisaccharide. According to one embodiment, pentose refers to sugar bound in polymer form that can be liberated or separated, such as with mild to moderate processing to break down the hemicellulose into simpler segments or monosaccharide units.

The remainder may include any suitable material, such as cellulose, lignin, remaining hemicellulose, soluble sugar, pectin, ash, and/or the like. Desirably, but not necessarily, the remainder may be consumed or used for producing energy. The remainder may be consumed or burned in a powerhouse or a boiler, such as for generation of heat or steam used in the processes. The steam may be processed in a turbine generator set to produce electricity, such as for the process or sold to the electrical distribution grid. Other uses of the remainder are within the scope of this invention. According to one embodiment, the remainder can be used to produce energy sufficient for the process or plant, such as to reduce utility costs. Desirably but not necessarily, the remainder may be dewatered and/or dried before combustion, such as to improve fuel value. In the alternative, the residue may be used for other purposes, such as compost, fertilizer, animal feed, landfill, and/or the like.

Converting broadly refers to altering the physical and/or chemical nature and/or properties of an object or item, such as in manufacturing. Converting may also include changing from one form or function to another. Converting may include an algae process, a bacterial process, a fungal process, a free enzyme process, any other suitable step to change a sugar into a biofuel, and/or the like.

According to one embodiment, converting to a butanol includes the use of fermentation processes, such as using yeast, bacteria, cyanobacteria, algae, enzymes, and/or the like. Fermentation broadly refers to a chemical change, such as with effervescence or release of gas. Fermentation may include an enzyme controlled aerobic or anaerobic breakdown of an energy-rich compound, such as a carbohydrate to carbon dioxide and an alcohol and/or an organic acid. In the alternative, fermentation broadly refers to an enzyme controlled transformation of an organic compound. Enzymes broadly refer biologically derived molecules that can catalyze or facilitate chemical reactions or transformations. Enzymes may be used alone (on their own) and/or in conjunction with other molecules, such as co-factors. Enzymes may include proteins, for example.

Suitable converting processes for butanol and/or biogasoline may include naturally occurring pentose consumers and/or genetically modified pentose consumers. Naturally occurring organisms may produce alcohols or other oxygen containing compounds, such as may be used directly or may be converted to an ether and/or the like. Genetically modified organisms may directly produce a biogasoline product. In the alternative, genetically modified organisms may produce an intermediate compound.

According to one embodiment, converting to a biodiesel material may include the use of fermentation processes, such as with yeast, bacteria, cyanobacteria, algae, enzyme, and/or the like. The converting the pentose to biodiesel material may include an algae process, a bacterial process, a fungal process, an enzyme process, a free enzyme process, a fermentation process, and/or the like. These suitable converting processes may include naturally occurring pentose consumers and/or genetically modified pentose consumers. Naturally occurring organisms may produce fatty acids, such as may be esterified with an alcohol, hydrogenated with hydrogen, and/or the like to produce a biodiesel product. Genetically modified organisms may directly produce a biodiesel product. In the alternative, genetically modified organisms may produce a fatty acid.

According to one embodiment, the remainder may be treated to breakdown or depolymerize the cellulose to form hexose and a reduced remainder. The reduced remainder may include remaining cellulose, lignin, remaining hemicellulose, remaining soluble sugar, pectin, ash and/or the like. The hexose from the cellulose may be converted to biogasoline and/or biodiesel in any suitable manner.

The hexose from the cellulose may be consumed in a fermentor, such as to produce biogasoline and/or biodiesel. Optionally, the hexose from the cellulose may be converted to biodiesel material, such as by the types and/or kinds of mechanisms or processes discussed above with respect to pentose conversion to biodiesel material. Desirably, but not necessarily, the hexose and the pentose streams remain separated, such as to not have competing reactions or competing food supplies in the converting processes or for the organisms. In the alternative, the hexose and pentose may be combined in a mixed fermentor with one or more biological processes to consume both sugars.

Hexose broadly refers to six (6) carbon member sugars or saccharides (monomers), corresponding disaccharides (dimers), corresponding trisaccharides (trimers), corresponding tetrasaccharides (tetramers), and/or the like. Hexose includes glucose, glacatose, sucrose, fructose, allose, altrose, gulose, idose, mannose, sorbose, talose, tagatose, any other isomer of six carbon sugars, and/or the like. Hexose may include and/or form complexes of relatively simple sugars, such as a disaccharide including sucrose, lactose, and maltose and/or a trisaccharide.

The remainder or reduced remainder may be dewatered and/or dried to improve fuel characteristics. The remainder or reduced remainder may be subjected to any other suitable pretreatment step, such as pH adjustment, mechanical processing, chemical processing, washing, liquid extraction, centrifugation and/or the like. The remainder or reduced remainder may be burned alone or may be consumed with supplemental fuel, such as coal or natural gas. The overall process and plant may be a net exporter or energy, such as selling electricity back to the electrical distribution grid.

According to one embodiment, the remainder and/or reduced remainder provides adequate energy for the complex so that no external or supplemental fuel is needed to meet energy needs.

Desirably, but not necessarily, the depolymerizing process may produce a relatively pure pentose stream as described above, such that pentose consumers do not preferentially consume hexose and reduce pentose conversion. The step of converting the pentose to butanol may include a single cell organism or microorganism process, such as may be easy to handle or process. In the alternative, the converting may include a multicell organism process. The converting the pentose to butanol may include an algae process, a bacterial process, a fungal process, a free enzyme process, any other suitable sugar consuming step, and/or the like.

According to one embodiment including biodiesel material as described below, the process may also include the step of reacting the biodiesel material with an alcohol-based material to form a biodiesel product and glycerin, and optionally the step of converting the glycerin to additional biodiesel material. The ester reaction may include reacting a triglyceride or fatty acid with an alcohol-based material to form an ester and glycerin or glycerol. The alcohol-based material may include any suitable alcohol, such as methanol, ethanol, propanol, butanol (all isomers), hexanol, and/or the like.

The alcohol for esterification may be made on site or coproduced, such as from a biological source. In the alternative, the alcohol for esterification may be brought in, such as from a third party supplier. The byproduct or output glycerin from the esterification process may be injected back into the process, such as food for organisms resulting in conversion to a fatty acid. In the alternative, the glycerin may be purified, if needed, and sold as commercial grade glycerin.

According to one embodiment, the alcohol-based material may include an alcohol derived from converting the hexose, such as from the cellulose in the remainder. Process integration may improve efficiencies. In the alternative, the biodiesel material may be hydrogenated to a hydrocarbon.

The step of converting the glycerin into additional biodiesel material may include returning the glycerin back to the step of converting the pentose to butanol and/or any other suitable step. Optionally, the glycerin may be consumed in the same or a separate fermentor as the other materials. In the alternative, the glycerin may be purified and sold as product glycerin, such as use in food, beverages, pharmaceuticals, cosmetics, munitions, polyurethanes, and/or the like.

According to one embodiment, this invention may include butanol and/or any other suitable biofuel made by any of the processes and/or plants described herein, such as butanol made by the process of depolymerizing pentose from a lignocellulosic feedstock to form a remainder and converting the pentose to a butanol. The butanol may include 1-butanol, 2-butanol, iso-butanol, and/or the like.

According to one embodiment, this invention may include a butanol plant for producing butanol from a lignocellulosic feedstock. The plant may include a lignocellulosic feed system and a pentose depolymerization unit adapted for removing pentose from the lignocellulosic feedstock to form a remainder. The plant may also include a pentose conversion unit adapted for converting pentose to a biofuel material.

Plant and/or production facility broadly refers to a collection of process equipment for performing a process, associated piping and/or conveyors, associated utilities, and/or the like, such as generally formed from one or more process blocks or units. Process blocks or units broadly refer to subparts or components of a plant, such as to accomplish or perform one or more specific tasks.

The lignocellulosic feed system may include any suitable process equipment and/or material handling devices, such as conveyors, belts, feeders, hoppers, drag chains, vibrators, chutes, silos, and/or the like. The feed system may further include any suitable mechanical equipment, such as cutters, choppers, roller mills, and/or the like. Other equipment may also be used in the feed system, such as for crushing, milling, pulping, pulverizing, washing, rinsing, diffusion processing, heating, adjusting pH, and/or the like.

According to one embodiment, the pentose depolymerization unit or removal unit may use or employ an acidic process, a basic process, an enzymatic process, a solvent process, and/or the like. The pentose conversion unit may include, use, and/or employ a single cell organism or a microorganism. The pentose conversion unit may use an algae process, a bacterial process, a fungal process, a free enzyme process and/or the like. The pentose conversion unit may use include algae, bacteria, fungus, free enzymes, and/or the like.

The plant may further include an esterification unit adapted to react the biodiesel material with an alcohol-based material to form a biodiesel product and glycerin, and optionally a line adapted for supplying the glycerin to the pentose conversion unit. Line broadly refers to any suitable transportation mechanism, such as a pipe, a pump, a gravity flow, a channel, a conduit, a duct, and/or the like.

According to one embodiment, the plant may further include a hexose depolymerization unit adapted for removing hexose from the remainder to form a reduced remainder, and a hexose conversion unit adapted for converting hexose to a biofuel material.

Any embodiment described herein as a process may also be embodied as a plant or production facility of corresponding structure and/or function. Similarly, any embodiment described herein as a plant may also be embodied as a process or method of corresponding step and/or function.

Any suitable combination of one or more biofuels or biofuel products are within the scope of this invention, such as pentose to butanol and/or biogasoline, pentose to butanol and/or biodiesel, pentose to butanol and/or biodiesel and hexose to butanol and/or biogasoline, pentose to biodiesel and/or butanol and hexose to biodiesel and/or butanol, and/or the like.

As used herein the terms "having", "comprising", and "including" are open and inclusive expressions. Alternately, the term "consisting" is a closed and exclusive expression. Should any ambiguity exist in construing any term in the claims or the specification, the intent of the drafter is toward open and inclusive expressions.

Regarding an order, number, sequence and/or limit of repetition for steps in a method or process, the drafter intends no implied order, number, sequence and/or limit of repetition for the steps to the scope of the invention, unless explicitly provided.

It will be apparent to those skilled in the art that various modifications and variations can be made in the disclosed structures and methods without departing from the scope or spirit of the invention. Particularly, descriptions of any one embodiment can be freely combined with descriptions or other embodiments to result in combinations and/or variations of two or more elements or limitations. Other embodiments of the invention will be apparent to those skilled in the art from consideration of the specification and practice of the invention disclosed herein. It is intended that the specification be considered exemplary only, with a true scope and spirit of the invention being indicated by the following claims.

What is claimed is:

1. A process for producing butanol from lignocellulosic feedstocks, wherein the lignocellulosic feedstocks include cellulose, hemicellulose, and lignin; the process comprising:
   depolymerizing pentose from hemicellulose in a lignocellulosic feedstock to form a remainder, wherein the remainder comprises cellulose and lignin;
   converting the pentose to butanol;
   depolymerizing hexose from the cellulose in the remainder without competing with pentose consumers; and
   consuming the remainder to produce energy.

2. The process of claim 1, wherein the lignocellulosic feedstock comprises bagasse, rice straw, corn stover, miscanthus, switchgrass, wheat straw, wood, wood waste, paper, paper waste, agricultural waste, municipal waste, sugarcane, energy cane, corn, maize, sorghum, sweet sorghum, sugar beet, or combinations thereof.

3. The process of claim 1, wherein the depolymerizing pentose from the lignocellulosic feedstock comprises an acidic process, a basic process, a solvent process, or combinations thereof.

4. The process of claim 1, wherein the converting the pentose to butanol comprises a microorganism process.

5. The process of claim 1, wherein the converting the pentose to butanol comprises an algae process, a bacterial process, a fungal process, a free enzyme process or combinations thereof.

6. The process of claim 1, wherein the butanol comprises 1-butanol, 2-butanol, or iso-butanol.

7. A butanol plant for producing butanol from a lignocellulosic feedstock, wherein the lignocellulosic feedstock includes cellulose, hemicellulose, and lignin; the plant comprising:
   a lignocellulosic feed system;
   a pentose depolymerization unit adapted for removing pentose from hemicellulose in the lignocellulosic feedstock to form a remainder, wherein the remainder comprises cellulose and lignin;
   a pentose conversion unit adapted for converting pentose to butanol;
   a hexose depolymerization unit adapted for removing hexose from the remainder to form a reduced remainder; and
   a hexose conversion unit adapted for converting hexose to a biofuel material.

8. The plant of claim 7, wherein the pentose depolymerization unit uses an acidic process, a basic process, a solvent process, or combinations thereof.

9. The plant of claim 7, wherein the pentose conversion unit uses a microorganism.

10. The plant of claim 7, wherein the pentose conversion unit uses an algae process, a bacterial process, a fungal process, a free enzyme process, or combinations thereof.

11. The plant of claim 7, wherein the pentose conversion unit and the hexose conversion unit comprise a single unit.

12. The plant of claim 7, wherein the pentose conversion unit and the hexose conversion unit comprise separate units.

13. The plant of claim 7, wherein the butanol comprises 1-butanol, 2-butanol, or iso-butanol.

* * * * *